US010415076B2

(12) United States Patent
Bellinzoni et al.

(10) Patent No.: US 10,415,076 B2
(45) Date of Patent: *Sep. 17, 2019

(54) HIGH THROUGHPUT QUANTIFICATION AND CHARACTERIZATION OF FOOT AND MOUTH DISEASE VIRUS AND PRODUCTS THEREOF

(71) Applicant: BIOGÉNESIS BAGÓ URUGUAY S.A., Montevideo (UY)

(72) Inventors: Rodolfo Cesar Bellinzoni, Tigre (AR); Nicolás Magi, Escobar (AR); Emmanuel Gérard Etienne Régulier, Vicente López (AR); Ana Romo, Chascomus (AR); Marcelo Arnolfo Spitteler, San Martín (AR)

(73) Assignee: BIOGÉNESIS BAGÓ URUGUAY S.A., City of Montevideo (UY)

( * ) Notice: Subject to any disclaimer, the term of this patent is extended or adjusted under 35 U.S.C. 154(b) by 0 days.

This patent is subject to a terminal disclaimer.

(21) Appl. No.: 16/053,906

(22) Filed: Aug. 3, 2018

(65) Prior Publication Data

US 2018/0346957 A1    Dec. 6, 2018

Related U.S. Application Data

(63) Continuation of application No. 14/730,418, filed on Jun. 4, 2015, now abandoned.

(60) Provisional application No. 62/009,126, filed on Jun. 6, 2014.

(51) Int. Cl.

| | |
|---|---|
| *C12Q 1/06* | (2006.01) |
| *G01N 30/60* | (2006.01) |
| *G01N 30/84* | (2006.01) |
| *G01N 15/02* | (2006.01) |
| *B01D 15/34* | (2006.01) |
| *G01N 30/46* | (2006.01) |
| *B01D 15/18* | (2006.01) |
| *C12Q 1/04* | (2006.01) |
| *G01N 30/74* | (2006.01) |
| *G01N 30/02* | (2006.01) |
| *G01N 15/00* | (2006.01) |
| *G01N 30/78* | (2006.01) |

(52) U.S. Cl.
CPC .......... *C12Q 1/06* (2013.01); *B01D 15/1864* (2013.01); *B01D 15/1885* (2013.01); *B01D 15/34* (2013.01); *C12Q 1/04* (2013.01); *G01N 15/0205* (2013.01); *G01N 30/468* (2013.01); *G01N 30/6043* (2013.01); *G01N 30/74* (2013.01); *G01N 30/84* (2013.01); *G01N 30/78* (2013.01); *G01N 2015/0065* (2013.01); *G01N 2030/027* (2013.01); *G01N 2030/8429* (2013.01); *G01N 2030/8435* (2013.01); *G01N 2333/005* (2013.01)

(58) Field of Classification Search
None
See application file for complete search history.

(56) References Cited

U.S. PATENT DOCUMENTS 10,041,103 B2 *  8/2018  Bellinzoni ......... G01N 30/6043

OTHER PUBLICATIONS

Spitteler et al. Vaccine 2011, vol. 29, pp. 7182-7187.*

* cited by examiner

*Primary Examiner* — Shanon A. Foley
*Assistant Examiner* — Myron G Hill
(74) *Attorney, Agent, or Firm* — Law Offices of Albert Wai-Kit Chan, PLLC

(57) ABSTRACT

The present invention provides a high throughput method to quantify and characterize the size and integrity of viruses and viral molecules. In one embodiment, the present invention provides a method to quantify and characterize size and integrity of Foot and Mouth Disease virus (FMDV) using chromatographic system and in-line Dynamic Light Scattering (DLS) technique. In one embodiment, the present invention further comprises a column-switching system for running multiple analyses simultaneously. The present invention also provides a method to develop and evaluate FMDV containing products for preventing Foot and Mouth Disease (FMD). In one embodiment, the methods described herein assess the stability of FMDV. In another embodiment, the methods described herein serve as in-process quality control for a manufacturing process of FMD vaccine.

10 Claims, 7 Drawing Sheets

−◯− Viral concentration (μg/mL)
··•·· Particle size (nm)
−✱− Cell count (x10⁶ cell/mL)

Time course of FMDV infection

HIGH THROUGHPUT QUANTIFICATION AND CHARACTERIZATION OF FOOT AND MOUTH DISEASE VIRUS AND PRODUCTS THEREOF

This application is a continuation application of U.S. Ser. No. 14/730,418, filed on Jun. 4, 2015, which claims the benefit of U.S. Provisional Application No. 62/009,126, filed Jun. 6, 2014. The entire contents and disclosures of the preceding application are incorporated by reference into this application.

Throughout this application, various references are referred to and disclosures of these publications in their entireties are hereby incorporated by reference into this application to more fully describe the state of the art to which this invention pertains.

FIELD OF THE INVENTION

The present invention relates to quantification and characterization of Foot and Mouth Disease virus (FMDV). The present invention further pertains to development of products to prevent Foot and Mouth Disease (FMD), and evaluation of products containing FMDV.

BACKGROUND OF THE INVENTION

Foot and Mouth Disease (FMD) is an acute systemic viral infection that affects food producing animals, such as cattle, sheep, goats, swine and other cloven-hoofed animals. Despite its very low mortality rate, the highly contagious nature of FMD makes it one of the most serious diseases of the livestock industry in terms of productivity losses and economic impact.

The disease is endemic in many parts of the world. The World Organization for Animal Health (OIE) periodically publishes disease distribution and outbreak maps. The sanitary status granted by the OIE has a profound economic impact in countries with meat trade-dependent economies because of the market restrictions that OIE imposes, especially on countries affected by FMD.

Effective vaccines and stringent control programs have eradicated the disease in most developed countries but, regardless of strict international trade policies, major outbreaks have occurred relatively recently in Europe (2000, 2001) and in Japan (2000, 2010).

Even though many countries have obtained the status of "free from FMD with vaccination" in some or all of their territory, the occurrence of outbreaks in neighboring countries represents a constant threat.

Despite continuous efforts to develop recombinant subunit vaccines that would not require propagation of the pathogen in large scale, current vaccines are based on inactivated whole virus concentrated and purified to reach a critical mass of antigen capable of generating a protective immune response. These vaccines are manufactured in plants with NBS biological safety level 4 (OIE). It is estimated that between 2.5 and 3 billion doses are produced annually worldwide.

Additionally, many countries have established emergency programs that include storage of frozen FMD antigens, called antigens banks, that would enable quick formulation of emergency vaccines in case of an FMDV pandemic.

The efficacy of inactivated virus vaccines, which are routinely used as part of eradication programs and in emergency contexts, is highly dependent on the antigenic payload formulated in each dose and on virus integrity.

The FMD virus (FMDV) is a non-lipid-enveloped virus featuring an icosahedral symmetry and a described size (diameter) ranging from 28 to 40 nm. The whole virus particle is extremely labile in vitro, it dissociates into monomers at temperatures above 56° C. and pH below 6. Seven FMDV serotypes have been reported, designated as O, A, C, SAT1, SAT2, SAT3 and Asia1.

The 140S (146S) quantitative sucrose density gradient analysis is the recommended method to quantify virus antigen and, on that basis, formulate vaccines. The 140S (146S) method, as developed by Barteling and Meloen (Barteling S J, Meloen R H. *A simple method for the quantification of* 140S *particles of foot-and-mouth disease virus (FMDV)*. Arch Gesamte Virusforsch, 1974; 45(4):362-4), has provided over the past three decades a reliable method for virus concentration measurement. The method consists of ultracentrifugation of the sample in a sucrose concentration gradient from about 20 to 45%. The sucrose gradients are prepared by layering sucrose solutions of decreasing concentration either by hand or using simple gradient mixers.

The principle of the 146S method is to separate the FMD viral particles based on their sedimentation coefficient in the sucrose gradient. Therefore, the technique provides only an indirect measurement of the integrity of the viral particles.

A number of international efforts have been attempted in order to standardize the method but there is as yet neither a harmonized protocol nor an international FMDV standard. The technical complexities of the method and the requirement of specialized items of equipment have probably contributed to this situation (Barteling S J. *Need for further standardization of the* 146-S *test as the basis for final-Foot-and-Mouth Disease (FMD) Vaccine formulation*. EUFMD Research Group Meeting 1999—Appendix 17).

The lack of a standardized method to measure the active ingredient present in FMD vaccines is an important factor to explain why expensive and cumbersome clinical trials, typically involving 17 to 20 large animals (the target species) per batch, are still required for registration of FMD vaccines and batch release.

Over the last decades, human and veterinarian health industries have witnessed increasingly stringent government regulations related to Good Manufacturing Practice (GMP) for the production of pharmaceutical and biopharmaceuticals products. New quality concepts have arisen, like Process Analytical Technology (PAT), which Food and Drug Administration (FDA) defines as a mechanism to design, analyze, and control pharmaceutical manufacturing processes through the measurement of Critical Process Parameters (CPP) that affect Critical Quality Attributes (CQA). PAT emphasizes the importance of controlling the production process as a means to achieve the highest quality standard for the final product.

For the vaccine industry and especially for vaccines based on full-size antigens (like inactivated viral vaccines or live attenuated viral vaccines), methods and equipment capable of reliably quantifying and determining the size of particles in the nanometer (nm) range would represent important tools for the implementation of in-process controls meant to ensure the quality of the viral antigens produced at every step of the process. Nevertheless, the analysis of complex process streams containing virus particles is a much more difficult task than the analysis of common recombinant proteins like monoclonal antibodies (mAbs). One challenge is that manufacturing practices for many current vaccines were developed decades ago, before the rise of serum-free media culture technology. The serum containing medium used in many manufacturing processes contains a very high content of proteins. Also, the yield of virus particles obtained from the infection of cell culture is generally in the order of milligram per liters, which is several orders of magnitude lower compared to the expression of recombinant proteins such as mAbs. Also of great importance is the fact that some viruses, like FMDV, have lytic replication cycle that triggers the destruction of the cell. The release in the cell culture medium of all the materials contained in the cytoplasm and the nucleus of the cells, including all the genomic material and lipid residues from the cell membrane will make the analysis more difficult.

Since size exclusion chromatography separates different molecules based on their hydrodynamic volumes, molecules of different molecular weights but similar hydrodynamic volumes are prone to show very similar mobility behavior during chromatography runs. In the conditions of very complex process streams, size exclusion chromatography is usually unable to provide a resolution good enough in order to separate the peak of virus particles of interest from other process contaminants of similar hydrodynamic volume such as large molecules of DNA and large lipid residues.

Protein or viral-based vaccines are vaccine models usually employed for delivering antigens to a subject for immunization. It is extremely crucial that the antigen being delivered is of its correct or native conformation such that appropriate epitopes can be presented to induce specific and effective immune responses. Therefore, misfolded, degraded or aggregated antigen may have reduced efficacy in, or even not be capable of, triggering specific immune responses. Dynamic Light Scattering (DLS) helps to assess the efficacy of protein or viral-based vaccines in terms of their integrity and stability. By analyzing the DLS profile, one would be able to check whether the antigens have been degraded or aggregated over time or upon storage in a particular buffer or temperature, and thereby assuring the efficacy of the vaccines.

Separation methodologies such as size-exclusion chromatography, when used alone, usually give rough estimates of particle size by close scrutiny of mobility behavior but these assessments are not sensitive enough to detect subtle modifications of antigen dimension. In contrast, DLS sensitively and accurately detects and estimates size of particles, and hence allows monitoring subtle differences of the particles' size. However, DLS can only analyze the integrity and estimate the size of particles with high purity.

Due to the economic relevance of FMD worldwide, there is a continuous need of improvements in the prevention tools, particularly regarding improved vaccines and/or methods of preparation thereof. The present invention provides methods for the quantification and characterization of FMDV and related products in a high-throughput and accurate manner. With the growing demand for both quantity and quality of FMDV vaccines, the present invention is a very useful and cost-effective tool for the quality control of the FMDV vaccines.

As an example, the world biggest FMD vaccine market, the Chinese market, requires 1.7 billion doses (of 2 milliliters each) per year. Considering that one average industrial batch of vaccine represents 5 million doses (i.e., a 10000 liters batch), this means that around 340 batches of FMD vaccines are produced each year in China by different manufacturers. As of today and because of this huge number of batches produced, the Chinese Veterinary Regulatory Authority has forfeited the responsibility of controlling the quality of the FMD vaccine batches and has to rely on the performance of quality control tests by each vaccine manufacturer. The quality control of FMD vaccines is usually monitored using in vivo potency testing which allows assessment of the quality of the vaccines in bulk quantity but requires complex and cumbersome procedures. Currently, there are no other in vitro techniques available that would enable the quality control of such a great quantity of batches of vaccine in a timely manner.

The present invention, for the first time, introduces an in vitro system that is capable of quantifying the antigen payload per dose and characterizing the size and the integrity of the inactivated antigen in each vaccine batch, in a high throughput manner. The present invention implements a much more simplified system than the in vivo potency testing system for the quality control of the FMD vaccines and thereby improves the quality of the products. It is estimated that the present invention can monitor the quality of 340 batches of vaccines in just a few days.

Thus, the present invention would eventually guarantee a better quality of the vaccines and confer a better protection against the Food and Mouth Disease to the animal population.

SUMMARY OF THE INVENTION

In order to improve current methods and products for prevention of Food and Mouth Disease, the present invention introduces a method for quantification and characterization of the Foot and Mouth Disease virus (FMDV) by a combined use of a molecular exclusion chromatography and an in-line dynamic light scattering detection (DLS) for analysis of the chromatographic profile. The method described herein can quantify and characterize FMDV with high throughput and accuracy.

In one embodiment, the present invention provides a method to quantify Foot and Mouth Disease Virus (FMDV) particles and to characterize their size and integrity in a complex process stream where some process contaminants cannot be separated from the FMDV particles by molecular exclusion chromatography only.

In one embodiment, the present method further comprises one or more sample preparation steps including a solvent extraction step using solvent such as chloroform, and an endonuclease digestion step using endonuclease such as Benzonase® before the molecular exclusion chromatographic method and dynamic light scattering analysis.

In one embodiment, the present invention provides a method for isolating and purifying FMDV particles from products containing the particles.

In one embodiment, the present invention provides a method for designing and preparing formulation of products to prevent foot and mouth disease.

In one embodiment, the present invention provides a method for evaluation of products containing FMDV such as the quantity and stability of antigens. These products include but are not limited to antigen banks and vaccine containing FMDV.

In one embodiment, the present invention provides a method serving as an in-process quality control tool for determining the quantity and characterizing the integrity and size of FMD antigens in intermediate products synthesized during the whole FMDV vaccine production process.

BRIEF DESCRIPTION OF THE DRAWINGS

FIG. 1A is the chromatographic profile tracked under 254 nm and FIG. 1B is the chromatographic profile tracked using Dynamic Light Scattering (DLS).

FIG. 2A is the chromatographic profile tracked under 254 nm and FIG. 2B is the chromatographic profile tracked using Dynamic Light Scattering (DLS).

FIG. 3A shows the chromatographic profile tracked under 254 nm of 2 samples: one sample treated with chloroform extraction and Benzonase® digestion and one sample without any treatment. FIG. 3B shows the chromatographic profile tracked under 254 nm of 2 samples both already treated with chloroform extraction: one sample further treated with Benzonase® digestion and the other sample without the Benzonase® digestion. FIG. 3C shows the chromatographic profile tracked under 254 nm of 2 samples both already treated with Benzonase® digestion: one sample further treated with chloroform extraction and the other sample without the chloroform extraction.

FIG. 4A shows the chromatographic profile tracked under 254 nm of an FMDV antigen concentrate obtained by ultrafiltration (UF). FIG. 4B shows the overlay of U.V. chromatographic profiles obtained from the five tested FMDV samples. FIG. 4C shows the chromatographic profile of two samples containing 20% or 80% of FMDV concentrate tracked by Dynamic Light Scattering (DLS).

FIG. 5 shows the plot of viral concentration (μg/mL) and virus particle size (nm) versus the percent of dilution with regression line.

FIG. 6 shows a time course plot of a FMD virus infection in a 2000 liters cell culture bioreactor. It shows the changes in viral concentration (μg/mL), cell count ($10^6$ cell/mL) and the size of viral particles (nm) during the first eight hours after the infection.

DETAILED DESCRIPTION OF THE INVENTION

Figure 1A:
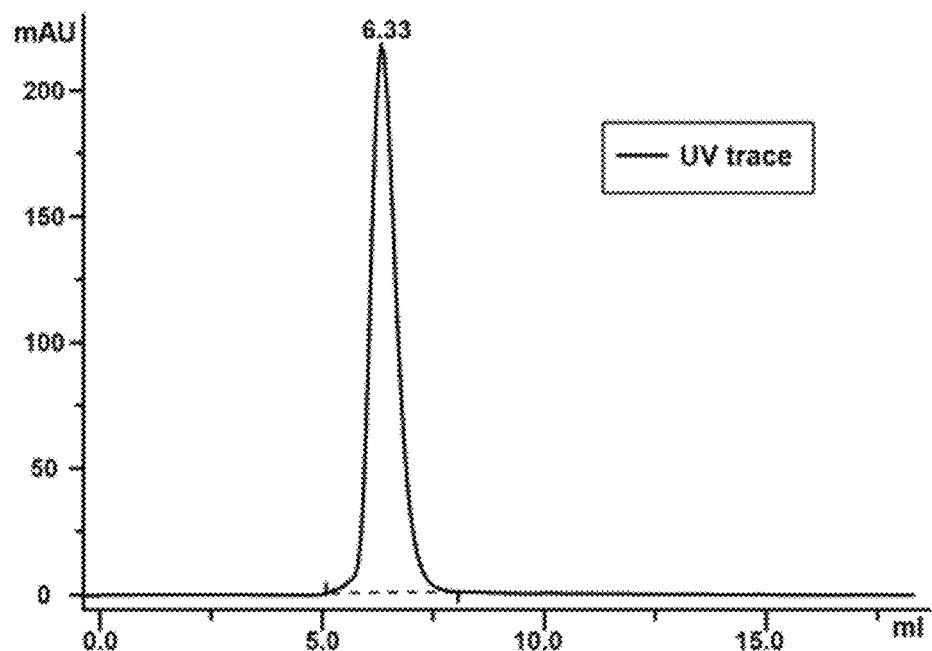
FIGS. 1A and 1B show one embodiment of the chromatographic profiles of purified O1 Campos FMDV.

The present invention provides a method for quantification and characterization of viruses such as the Foot and Mouth Disease virus (FMDV) with high throughput and high accuracy.

With the combined use of two samples preparation steps of a solvent extraction and an endonuclease digestion with molecular exclusion chromatography, and a chromatographic profile analysis carried out by means of UV absorption at 250-280 nm and Dynamic Light Scattering (DLS) detectors, the method of the present invention provides an unexpectedly improved method for quantification and characterization of the integrity and size of FMDV particles at every step of the manufacturing process of a FMD vaccine. The two sample preparation steps facilitate the separation of molecules and allow a high-throughput quantification and characterization of FMDV from all sources including the very complex process streams. Size exclusion chromatography (SEC) alone would not be able to separate the virus particles from contaminants such as large DNA molecules or large lipid residues that appear in these complex processes because these contaminants usually have hydrodynamic volumes similar to that of the FMDV. Also, the present method is advantageous over using size exclusion chromatography (SEC) alone for the characterization of the FMDV antigens since the latter can only provide an indirect and rough estimate of size based on elution volume from the chromatographic column.

The method of the present invention allows a rapid and accurate assessment of both the concentration and the quality of the FMDV antigens, wherein the quality is defined based on the structural integrity and size of the virus particles. With the more precise and accurate measurement by Dynamic Light Scattering (DLS) as compared to the 146S traditional sucrose gradient technique, the method described herein enables a more accurate estimation and a direct control of integrity and size of the viral antigens.

Calibrated SEC columns packed with chromatography media of a pore size that allows partial access of protein molecules, protein fragments and aggregates to the internal volume of the media can be used in order to assess polymerization and molecular fragmentation of highly purified proteins or peptides in biopharmaceutical preparations and products. However, DLS can only be used to analyze the integrity and size of particles with high purity. These techniques are not readily applicable in a high throughput format to more complex proteins solutions or in crude process intermediates that contain other kinds of contaminants like DNA or lipid molecules. It is because the limited resolution of the SEC in a short chromatographic run would not allow a sufficient separation of peaks of different species in the solution and therefore would not allow a good characterization of the sizes of different molecules. SEC-DLS and SEC-MALS (Multi-Angle Light Scattering) techniques have been reported to quantify and characterize highly purified virus particles and virus-like particles (VLPs) but not virus particles in crude or complex samples. The present invention, on the contrary, can be applied successfully to all kind of samples during the whole manufacturing process of virus particles or vaccine, and samples from other sources or processes. Examples include but are not limited to: a) during the infection of the cells cultured in a bioreactor (see Example 6) where the virus concentration is very low and the level of process contaminants is very high (e.g. proteins from bovine serum, proteins from lysed cells, cellular DNA and lipid residues released due to cellular membrane destruction); b) after the concentration of antigens in which the concentration factor can be as high as 150× or higher (see Example 5); c) before formulation of the final vaccine in order to determine the appropriate payload of each vaccine dose, and d) on the final formulated product even in the cases of vaccines formulated as a water-in-oil emulsion (W/O) or water-in-oil-in-water double emulsion (W/O/W). The quantification and characterization technique described in the present invention can be applied to intermediate samples taken from very complex and crude processes as well as to highly purified FMDV reference standard with the same efficacy, accuracy and high throughput.

In one embodiment, the method of the present invention enables the analysis of both the quantity and the quality (e.g. integrity and size) of up to about 60 to about 70 samples of FMDV per day, a significantly higher throughput that is impossible to obtain in the case of employing other technique like Fast Protein Liquid Chromatography (FPLC) because of time constraints due to the long duration of one sample run (e.g. 3 hours) on the FPLC equipment. Therefore, the use of FLPC equipment allows a processing of a maximum of 4 samples per working day. On the other hand, the traditional 146S technique only allows for the analysis of a maximum of 12 samples per working day.

The method of the present invention is very significantly different from the prior techniques, because it can be applied successfully to samples prepared from all kind of processes including crude intermediates and purified viral samples, because it includes an in-line DLS detector that provides a direct estimation of integrity and size of the virus particle in question and can be run in a high throughput format.

In one embodiment, the present invention provides a multi-column switching mechanism that can be used in combination with the present methods or other applicable methods to further achieve a high samples throughput (see Example 7). In one embodiment, the present invention provides a column-switching system which is capable of running multiple columns and DLS detectors at the same time for a high throughput analysis. On the contrary, it is not feasible to implement the same technique in the case of the FPLC because FPLC usually involves a long duration of run, e.g. 3 hours per run.

Any change in the 3-dimensional structure especially in relation to the important epitopes of the antigen may decrease the immunogenicity of the antigen. The method of the present invention also enables a characterization of the antigen with high sensitivity, since it allows detection of small changes in the diameter of the viral antigens particles being quantified, while those small changes would be totally impossible to be detected with the traditional techniques such as sucrose gradient 146S technique, or chromatography alone. Therefore, the present invention is capable of detecting small alterations in the size of antigens and provides a huge improvement for the characterization of the quality of an antigen.

In one embodiment, the present invention provides a method for quantification and characterization of whole Foot and Mouth Disease Virus (FMDV) by high-performance liquid chromatography (HPLC). In one embodiment, the method comprises injecting a FMDV sample into a chromatographic column, eluting the sample, analyzing the chromatographic profile at a predetermined elution time range and determining the quantity, integrity and size of FMDV particles.

In one embodiment, the chromatographic column is a molecular exclusion chromatography column.

In one embodiment, the chromatographic column is designed to separate particles with sizes in the range of 20-200 nm or higher and molecular weights in the range of $10^5$-$10^9$ Dalton or higher.

In one embodiment, the predetermined elution time range is resolved by the chromatographic run of reference or standard samples of purified FMDV.

In one embodiment, the method described herein can quantify FMDV antigens or particles in a concentration range that is much broader than that attained by the current technologies, i.e. 5 to 70 µg/mL or 3 to 300 µg/mL. In another embodiment, the present method can quantify FMDV antigens or particles within the concentration of 1.2 to 750 µg/mL. In another embodiment, the present method can quantify FMDV antigens or particles higher than 750 µg/mL.

In one embodiment, the method described herein can characterize with great accuracy the size and integrity of FMDV antigens or particles independently of the concentration of the virus particles. It has been tested empirically using an in-line DLS that, the present method can accurately measure the size of FMDV samples having a concentration ranging from 1.2 to 750 µg/mL, and the measurement is independent of the concentration of the FMDV antigens (see Examples 5 and 6). These results represent the first report of an accurate size and integrity characterization of FMD virus by an in-line DLS over such a broad range of concentrations.

The UV quantification of the present method was thoroughly validated with regard to reproducibility, specificity, linearity, accuracy, precision, and robustness. It represents the first validated technique available for the quantification of FMDV particles that also characterizes in-line the integrity and the size of the particles quantified. Since FMDV has a large size as compared to most components in a purified or crudely purified sample, FMDV may be isolated from low molecular weight components in the sample using conventional SEC techniques and eluted in the exclusion volume (or the void volume) of the column or very close to it, depending on the type of size exclusion column used. However, some high molecular weight components like large DNA molecules or lipid residues cannot be separated by SEC alone as these molecules have very similar hydrodynamic volume compared to FMDV particles. In addition, SEC or similar technologies cannot differentiate FMD viruses that are slightly different in sizes. It is because the FMD virus is nearly excluded from the pores of the SEC and straightly passes through the column. Elution volumes of FMD viruses of different sizes can be very similar. Offline DLS is of limited value to ascertain viral particle size because its results are strongly influenced by polydispersity. The presence of bigger and smaller particles in the sample may greatly affect the results. On the other hand, the combined use of DLS and SEC-HPLC relies on the high purity of the chromatographic peak to produce a direct particle size measurement unencumbered by other sample components; such size measurement cannot be inferred from the chromatographic mobility.

In one embodiment, the chromatographic profile analysis is carried out by means of UV absorption at 250-280 nm and Dynamic Light Scattering (DLS) detectors. In another embodiment, the chromatographic profile analysis is carried out by means of in-line Dynamic Light Scattering (DLS) detectors. The present method features an in-line Dynamic Light Scattering detector that enables a direct and real-time analysis of the whole size exclusion chromatographic profiles and thereby allows a rapid and accurate assessment of both the concentration and the quality of the FMDV antigens.

In one embodiment, the chromatographic profile analysis of an FMDV sample is carried out by a comparison to a predetermined size distribution of integral viral particles. Reference or standard samples containing purified FMDV are analyzed by chromatography and in-line DLS analysis, thereby resolving the sizes of each FMDV strain and generating predetermined size distribution of FMDV particles.

In one embodiment, the chromatographic profile analysis of a purified sample allows differentiation of whole integral viral particles from disintegrated FMDV fragments, e.g. 12S particles or capsomers.

In another embodiment, the chromatographic profile analysis enables a detection of size deviation (e.g. in a range from 20 to 60 nm) of viral particles in an FMDV sample as compared to the reference sample(s) of the same strain.

In one embodiment, the chromatographic profile analysis enables quantification and characterization of size and integrity of FMD viral particles of up to 57 samples per working day. In one embodiment, the chromatographic profile analysis enables quantification and characterization of size and integrity of FMD viral particles of up to 72 samples per working day.

In one embodiment, the FMDV sample includes, but not limited to, a supernatant of an FMDV infected cell culture, an intermediate product from the vaccine manufacturing process, an antigen batch or bank, a vaccine, a monovalent vaccine batch or a multivalent vaccine batch.

In one embodiment, the FMDV sample is optionally pre-treated with a solvent prior to the injection into the chromatographic column. In one embodiment, solvent used herein is a non-polar or a lipid-soluble solvent including, but is not limited to, chloroform, benzene, toluene, hexane, pentane and octane. In one embodiment, solvent used here is a polar organic solvent including, but is not limited to, methanol, ethanol, isopropanol, dichloromethane, acetone and acetonitrile. In one embodiment, one or more types of solvent are used together for pre-treating the samples.

In one embodiment, the FMDV sample is optionally pre-treated with one or more enzymes prior to the injection into the chromatographic column. In one embodiment, the enzyme is a nuclease including but not limited to a DNase, RNase, endonuclease, exonuclease and restriction endonuclease. In one embodiment, the enzyme is Benzonase®, TURBOT DNase, T7 endonuclease, S1-nuclease, P1-nuclease, or Endonuclease I. The nuclease cuts the large DNA molecules into smaller DNA molecules which can be subsequently separated by the chromatographic column.

In another embodiment, the monovalent vaccine or multivalent vaccine is pre-treated in order to remove adjuvants prior to the optional treatment with a nuclease.

In one embodiment, the reference or standard sample(s) of purified FMDV for each strain are prepared by infecting a mammal cell culture with FMDV, inactivating the produced virus with a chemical agent, and one or more of: ultracentrifugation on sucrose gradient, ultrafiltration, ion exchange chromatography or molecular exclusion chromatography.

In another embodiment, the reference or standard sample of purified FMDV is prepared by removing the adjuvant from a reference vaccine.

In one embodiment, the present invention provides a method for isolating and purifying FMDV particles from products containing the particles.

In another embodiment, the present invention provides a method of in-process quality control for determining the quantity and characterizing the integrity and size of the FMDV antigens produced at every step of the manufacturing process of an FMD vaccine. With a combined use of size exclusion chromatography and in-line DLS detection, the present invention also provides a tool for monitoring the kinetics of infection during the production process of the viral antigen (see Example 6). By checking both the quantity and the quality (e.g. integrity and size) of the live virus, the present invention enables a high-level of in-process control, in accordance with the international guidelines of Process Analytical Technologies (PAT) which is the highest quality standard in the production of veterinary vaccine.

In one embodiment, the present method is capable of detecting whether the FMDV products are contaminated by other viruses. Sometimes, cells used for the production of FMDV may be contaminated by other viruses or pathogens which can also propagate in the culture bioreactor. SEC alone may not be able to remove or even detect the contaminating viruses since most viruses are large in size, and therefore both the FMDV and the contaminating viruses will be eluted at the exclusion volume of the column. In contrast, the present invention is capable of detecting the presence of contaminating viruses or other pathogens that have a different size than the FMDV by analyzing the DLS profile. For example, viruses that are larger than the FMDV will lead to an increase in dispersed light intensity and/or Z-average in the peak. It is also possible to quickly assess the degree of contamination by comparing the DLS profiles of the contaminated and non-contaminated samples.

In one embodiment, the present method is used to assess if significant variations exist between various batches of FMDV vaccines or products by comparing their U.V. and DLS profiles. A constant set of U.V. and DLS profiles would indicate the process stream is normal and the quality of products is maintained. Any detectable differences in the U.V. or DLS profiles may indicate an error or a deviation from the normal process stream or a possible contamination. This would ultimately provide a better quality control to ensure the consistent quality and efficacy of the products.

In another embodiment, there is provided a method for evaluating FMDV antigen-containing products by determining the stability of the FMDV antigen. The evaluation method comprises quantification and characterization of the integrity and size of FMDV particles in a sample at two different time points by means of the method of the present invention and quantification of changes occurred in the sample and deviation in size and/or integrity of the viral particles during the two time points in order to measure the stability of the FMDV antigen. The present method can also be used to characterize viral particles stored at different temperatures or in different buffers or formulated with different adjuvants.

In another embodiment, the present invention provides a method to evaluate and prepare a vaccine against Foot and Mouth Disease, either monovalent or multivalent. By using the method described herein, quantification of the antigenic payload per dose and characterization of the integrity and size of the antigens formulated in the vaccine can be performed.

The present invention provides a method for quantification and characterization of Foot and Mouth Disease Virus (FMDV), comprising the steps of (a) treating samples comprising FMDV with one or more enzymes to obtain a plurality of FMDV samples; (b) applying a first FMDV sample to a chromatographic system comprising a plurality of pumps and a plurality of chromatographic columns, wherein (i) a first pump is connected to a first chromatographic column via a first valve, said first column is further connected via a second valve to a detection system comprising a U.V. detector and a Dynamic Light Scattering (DLS) detector; and (ii) a second pump is connected to a second chromatographic column via said first valve, said second column is further connected via said second valve to a waste collector, wherein the first FMDV sample is run through the first column while a washing buffer is run through the second column; (c) eluting the first FMDV sample from the first column and obtaining chromatographic profiles for quantification and characterization of the first FMDV sample by said detection system; (d) switching connections for said first and second pumps so that (i) said first pump is now connected to said second column via said first valve, said second column is further connected via said second valve to said detection system; and (ii) said second pump is now connected to said first column via said first valve, said first column is further connected via said second valve to a waste collector, (e) applying a second FMDV sample to the second column while applying a washing buffer to the first column; (f) eluting said second FMDV sample from said second column and obtaining chromatographic profiles for quantification and characterization of said second FMDV sample by said detection system; and (g) repeating the steps of (b) to (f), thereby obtaining quantification and characterization of said plurality of FMDV samples.

In one embodiment, the enzymes used in the above method are nucleases such as exonuclease, restriction enzyme, DNase or RNase. In one embodiment, the FMDV sample can be a supernatant of a FMDV-infected cell culture, an intermediate product from a vaccine manufacturing process, an antigen batch or bank, a vaccine, a monovalent vaccine batch or a multivalent vaccine batch.

In one embodiment, the samples comprising FMDV are treated in a solvent before the chromatographic separation. In one embodiment, the samples comprising FMDV are treated in a solvent before or after the samples have been treated by enzymes such as nucleases. In one embodiment, the solvent is a non-polar such as chloroform, benzene, toluene, hexane, pentane or octane.

In one embodiment, the present chromatographic system comprises two chromatographic columns. In another embodiment, the present chromatographic system comprises three chromatographic columns.

In one embodiment, the chromatographic system further comprises an autosampler to inject the FMDV samples to the chromatographic columns. In another embodiment, the chromatographic system further comprises one or more systems to integrate and control the functioning of the plurality of components of the chromatographic system.

In one embodiment, the above quantification and characterization of FMDV samples comprise determining the size and integrity of said FMDV.

In one embodiment, the chromatographic columns are designed to separate particles with sizes in the range of 20-200 nm or higher and molecular weights in the range of $10^5$-$10^9$ Dalton or higher. In one embodiment, the concentration of FMDV particles present in the sample is from about 1.2 to about 750 μg/mL. In another embodiment, the above method is capable of analyzing the chromatographic profiles of up to about 60-70 samples per day.

In one embodiment, the above chromatographic profile is compared to a chromatographic profile derived from a reference or standard sample of purified FMDV. In another embodiment, the chromatographic profile is compared to a chromatographic profile derived from whole integral viral particles to allow differentiation of whole integral viral particles from disintegrated FMDV fragments.

In one embodiment, the above method separates large DNA molecules, lipid molecules and FMDV particles having similar elution volumes as eluted from the chromatographic column.

The present invention also provides a system for high-throughput quantification and characterization of samples containing Foot and Mouth Disease Virus (FMDV) particles, comprising an autosampler for sample injection; two or more chromatographic columns for separating the FMDV particles, wherein the two or more chromatographic columns are of the same type or of different types; two or more pumps for driving the two or more chromatographic columns; at least one ultraviolet detector for producing a chromatographic profile of the eluted FMDV particles and determining the quantity of said eluted FMDV particles; at least one Dynamic Light Scattering (DLS) detector for determining the size and integrity of the eluted FMDV particles; a waste collector for collecting liquids eluted from the chromatographic columns; and a multiple-valve array comprising two or more valves to connect the plurality of components of the system.

In one embodiment, the above system analyzes the chromatographic profiles of FMDV particles, eluted sequentially from each of the two or more chromatographic columns, thereby determining the quantity, size and integrity of the FMDV particles in a high-throughput and real-time manner. In another embodiment, the system further comprises one or more control systems for integrating and controlling the functioning of the plurality of components of the system.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Throughout this application, various references or publications are cited. Disclosures of these references or publications in their entireties are hereby incorporated by reference into this application in order to more fully describe the state of the art to which this invention pertains. It is to be noted that the transitional term "comprising", which is synonymous with "including", "containing" or "characterized by", is inclusive or open-ended and does not exclude additional, un-recited elements or method steps.

Example 1

Preparation of Reference Samples of FMDV

This example illustrates the procedure for preparing reference samples of FMDV for generating predetermined volume (or time) of elution and predetermined size distribution of FMDV particles.

Solutions used:
Dialysis membranes conditioning buffer:
Volume: 1 L
Composition: 10 mM NaHCO$_3$; 1 mM EDTA.
Dialysis buffer:
Volume: 5 L
Composition: 100 mM NaCl; 50 mM Tris Base; pH=8
Tris Buffer:
Volume: 5 L
Composition: 200 mM NaCl; 20 mM Tris Base; pH=8
Viral suspension:
Volume: 200 mL
Composition: FMDV strain 01 Campos
Procedures:
Step 1: Dialysis
This step was performed to reduce the ionic strength of the suspension of the virus to allow subsequent enzymatic digestion, without increasing the volume of the sample.
1. Boiled the dialysis bags in the dialysis membranes conditioning buffer for at least 30 minutes in a glass beaker. Rinsed 5 times with water and stored at 4° C. until use.
2. Closed the lower end of the dialysis bags and fill in samples.
3. Dialyzed the viral suspension samples four times against 800 mL of the dialysis buffer at 4° C. for 2 hours each time.
4. Dialyzed the viral suspension samples against 1800 mL of the dialysis buffer 4° C. for overnight.
Step 2: Enzymatic Digestion
This step was performed to remove nuclease-sensitive impurities from the samples.

1. Enzyme Preparation: at the time of use, diluted 25 μL Benzonase® (250 U/μL) in 10 mL of dialysis buffer preheated to 37° C. Final concentration of the enzyme dilution: 25 μL×250 U/μL=6250 U/10 mL=625 U/mL of Benzonase®.
2. Digestion: Fractionated the dialyzed viral suspension into centrifuge tubes of 50 mL, at 24 mL per tube. Added to each tube 1 mL of the enzyme dilution. Sealed the tubes and placed the tubes horizontally in an orbital platform shaker preheated at 37° C.
3. Stirred the samples sufficiently for 2 hours for a good agitation of the suspension, but avoid foaming.

Step 3: Desalting by Gel Permeation Chromatography

This step was performed to exchange buffer of the reference samples and eliminate low molecular weight components from the reference samples.

1. Equilibrated Sephacryl S-300 media with two washes of 500 mL of Tris buffer and re-suspend the media in a final volume of 230 mL. The total volume of packed resin was 150 mL and the total volume of the preparative column was 250 mL.
2. Packed the preparative column chromatography with equilibrated Sephacryl S-300 resin:
   a. Poured 230 mL of the suspension into the column.
   b. Allowed the resin to decant by gravity overnight.
   c. Placed the metallic mesh disc on the gel.
   d. Added 25 mL of Tris-Salts buffer on the metal mesh.
   e. Connected the reservoir with Tris buffer.
   f. Passed 200 mL of the buffer to the reservoir.
   g. Disconnected the reservoir from the Tris buffer.
   h. Opened the drip of the column until the buffer just reached the level of the mesh and then closed the drip.

Desalting/Elimination of low molecular weight components:
   a. Loaded 43 mL of sample onto the gel.
   b. Opened drip and allowed the sample to enter the gel.
   c. Loaded column with 60 mL of Tris buffer. Opened drip and collected the eluate containing the virus. Stored the eluate at 4° C.
   d. Equilibrated the column with 300 mL of Tris buffer.
   e. Repeated above until you finished passing all the samples. If the final sample volume to be loaded in the column is less than 43 mL, make up the sample volume to 43 mL with Tris buffer before loading it to the column.
   f. Prepared a pool of collected eluates.
   g. Performed a final column wash with 300 mL of Tris buffer. Unpacked the column and washed the resin two times with 500 mL of 20% ethanol each time.

Step 4: Evaluation of Reference Samples

Eluates obtained from step 3 were subject to sucrose gradient centrifugation, UV spectrophotometric titration and size exclusion chromatography to evaluate whether a purified sample of FMDV particles has been prepared.

Example 2

Quantification and Characterization of FMDV Particles

This example illustrates one embodiment of the present invention for quantifying and characterizing the integrity and size of FMDV particles in intermediate process samples, independently of their purity, and in the finished product, the FMD vaccine, using Dynamic Light Scattering (DLS). In one embodiment, the U.V. trace is used to determine the peak area for calculating the viral concentration, whereas the DLS is used to characterize the size and integrity of viral particles.

Equipment and Operating Conditions:
Infinity Agilent 1260 chromatograph equipped with pump, online degasser, autosampler, sample cooling module, column thermostat, UV detector of variable wavelength and PC Edition OpenlabCDS Chemstation software.
Chromatography column: TOSOH Bioscience TSKgel G4000PWXL (7.8 mm ID×30.0 cm L) or equivalent optionally equipped with guard column TSKgel PWXL Guardcol (6.0 mm ID×4.0 cm L) or equivalent and cartridge Phenomenex SecurityGuard GFC AJO-4489-4000.
Eppendorf Thermomixer Interchangeable block for 24×1.5 mL block.
GPC1 mobile phase (30 mM Tris, 400 mM NaCl, pH=8).
Benzonase®, Sigma E1014-25KU-≥250 units/μL, ≥90% (SDS-PAGE).
Benzonase® dilution buffer (50 mM Tris, 20 mM NaCl, 2 mM $MgCl_2$).
Working dilution of Benzonase® (1.25 U/μL).
Dilution Buffer 30 mM Tris, pH=8.
Malvern Zetasizer Nano S Dynamic Light Scattering (DLS) ZEN1600 analyzer with Zetasizer v. 7.02 software.
Flow-mode operation kit with flow cell Hellma Analytics 176.751-QS ZEN0116.

Analysis Procedure:
a) Pre-Treatment of Samples
i. Chloroform Extraction
(1) Supernatants of Cell Culture Infections, Aqueous Phase Before Formulation of the Emulsion and Ultrafiltration Concentrates.

5 mL of sample were fractionated into 15 mL centrifuge tubes and 5 mL of chloroform were added. Samples and chloroform were vigorously shaken for 2 minutes and then centrifuged at 4500 RPM for 15 minutes at 4° C. Aqueous upper layer was transferred to a fresh 15 mL tube. Chloroform extraction was repeated for a second time and upper layer recovered again into yet another fresh tube. For ultrafiltration virus concentrates a further dilution was performed adding 1 mL of a Tris 30 mM, pH=8 solution to 2 mL of chloroform extracted sample in order to reduce the sample ionic strength before enzymatic digestion.

(2) Viral Concentrates Prepared by PEG Precipitation.

10 mL of viral concentrate was sampled under constant vigorous magnetic stirring to keep precipitate from settling. The sample was transferred to a 250 mL beaker and diluted to a final volume of 100 mL with 30 mM Tris, 100 mM NaCl, pH=8 and magnetically stirred overnight at 4° C. 5 mL of the diluted concentrate was submitted to the chloroform extraction as described in the previous paragraph.

(3) Water-in-Oil Emulsion FMD Vaccine.

20 mL of commercial oil-based vaccine were fractionated in a 50 mL centrifuge tube. 20 mL of chloroform were added to the tube; it was shaken vigorously for 5 minutes and then centrifuged at 4500 RPM for 15 minutes at 4° C. The aqueous phase was separated and transferred to another 50 mL tube. A second portion of 20 mL of chloroform was added to the tube, shaken vigorously for 5 minutes and centrifuged at 4500 RPM for 15 minutes at 4° C. The aqueous phase was separated and transferred to another 50 mL tube. This recovered aqueous phase is the sample to be analyzed for water-in-oil emulsion FMD vaccine.

ii. Enzymatic Digestion

The recovered samples can be used directly or subject to pretreatment as described in the previous section, when appropriate. 1 mL of the sample obtained in the recovery procedure (i) was transferred to a 1.5 mL Eppendorf tube. 20 µL of working dilution of Benzonase® (1.25 U/µL) i.e. 25 U of Benzonase® were added to the tube, and it was shaken at 37° C. at 1400 RPM (high speed) in Eppendorf Thermomixer for 60 minutes. The sample tube was removed from the Thermomixer and centrifuged at 16000 g at 4° C. for 10 minutes. The supernatant was harvested from the tube, taking care of not disturbing the pellet, and loaded into a HPLC vial which was finally capped. Reference or calibration sample(s) prepared as described above was used directly or pre-treated in the same manner as the tested samples before performing chromatographic analysis. The temperature regulated, microprocessor-controlled, high-speed orbital mixer for microcentrifuge tubes from Eppendorf allows performing enzymatic digestion for up to 24 digestions simultaneously with the reduced sample volume requirements of HPLC.

b) Chromatographic Analysis

The sequence of samples to be injected was scheduled with the appropriate method for each sample type. The chromatographic elution line was connected: samples were run through the chromatography column, the U.V. detector and then the Hellma flow cell in the ZEN1600 DLS analyzer. Appropriate playlist was set in the Zetasizer software of the DLS analyzer. The peak of virus with a retention time of approximately 15 to 16 minutes (or corresponding volume of elution) was integrated (the exact time depends on the chromatographic elution conditions used). Concentration of FMDV in the control samples was determined according to the following equation:

$$FMDV[\mu g/mL]=(Area \times 10 \times 1.02)/(F_t \times 72 \times b \times Vol_{inj})$$

Where:
Area: is the area under the curve. It may have units of mAU*s, mAU*min or mAU*mL
10: is a unit conversion factor.
1.02: is a dilution correction factor for Benzonase solution addition, if applicable.
72: is the published mass absorptivity coefficient $_{254}E^{1\%}$ of FMDV.
$F_t$: is the flow-time factor, equal to 120 for Area in mAU*s, 2 for Area in mAU*min and 1 for Area in mAU*mL for a 0.5 mL/min chromatographic flow.
b: is the optical path length of the U.V. flow cell in cm.
$Vol_{inj}$: is the injected volume in mL.

For the ultrafiltration virus concentrates the result was multiplied by a factor of 1.5 to take into account the ⅔ dilution required before enzymatic digestion.

The plot Flow Trace vs. Volume/Time plot was generated in the DLS Zetasizer software. The FMDV peak signal was identified by its elution time/volume and the Z-average diameter (d·nm) of the peak was recorded.

The validity of the whole analysis procedure was confirmed by the following parameters: a) the slope of the calibration curve, obtained with the control samples, was 86.4 (mAU*s)/(mg/mL)±8.64; b) the absolute value of the x-intercept was less than 10% of the average concentrations of the control samples and c) the FMDV peak Z-average diameter is between 28 and 40 nm.

In one embodiment, the present method is validated based on parameters such as selectivity, peak purity, accuracy, linearity of response, repeatability, intermediate precision and limits of detection and quantification determined from FMDV reference or standard samples of the same viral strain. In one embodiment, two reference or standard samples each representing a high or a low quantity of FMDV are included in every test for validation purposes.

In one embodiment, one or more virus-free negative controls such as a mammalian cell sample which has been lysed by freeze/thaw cycles and pre-treated similarly as the FMDV samples were included in the test to validate the result.

Once the test was confirmed valid, the value of the tested samples was determined by direct calculation or by extrapolation of the area value obtained in the calibration curve established with the control samples.

In one embodiment, the length of column used in the present invention is 30 cm. In general, a shorter column provides a shorter run but a lower resolution especially for particles with similar hydrodynamic volumes. One of ordinary skill in the art can adjust the length of column according to type of samples of interest.

In one embodiment, a TOSOH Bioscience TSKgel G4000PWXL size-exclusion column is used to sufficiently isolate the FMDV particles from the contaminants in a short chromatographic run. Depending on the nature of the samples, resins of other pore sizes or in other forms or materials can be used to prepare the present size-exclusion column. However, it should be noted that, the pore size of resin does not only affect the resolution of the separation but also affect the total run time. For example, it would take a longer time to elute the FMDV if the pore size is big enough for the virus to enter, and therefore lengthen the whole separation process.

Interpretation of Results

Analysis of Purified O1 Campos FMD Virus Reference Sample and Evidence of its Disintegration after Heat Treatment This example shows direct evidence on how the method of the present invention enables quantification and the characterization of the integrity and size of FMD virus particles.

This example shows as well how the method of the present invention could detect fragments (12S or capsomers) of the disintegrated particles after the heat treatment and nuclease (Benzonase®) digestion of the purified O1 Campos FMDV reference sample.

FIG. 1A shows the chromatographic profiles at U.V. 254 nm of purified O1 Campos FMDV. The chromatographic profile shows a single peak with an elution volume of 6.33 mL. Calculation of the virus concentration based on the area under the curve yielded a concentration of 421.7 µg/mL, using the formula: FMDV [µg/mL]=(Area[mAU*mL]×10)/(1×72×0.5 [cm]×0.1 [mL]). Table 1 lists the parameters output from the UV chromatographic analysis of the elution peak.

TABLE 1

Chromatographic parameters of purified O1 Campos FMDV

| Peak | Elution Volume (ml) | Area (mAU * ml) | Height (mAU) |
|---|---|---|---|
| 1 | 6.33 | 147.1057 | 217.037 |

Figure 1B:
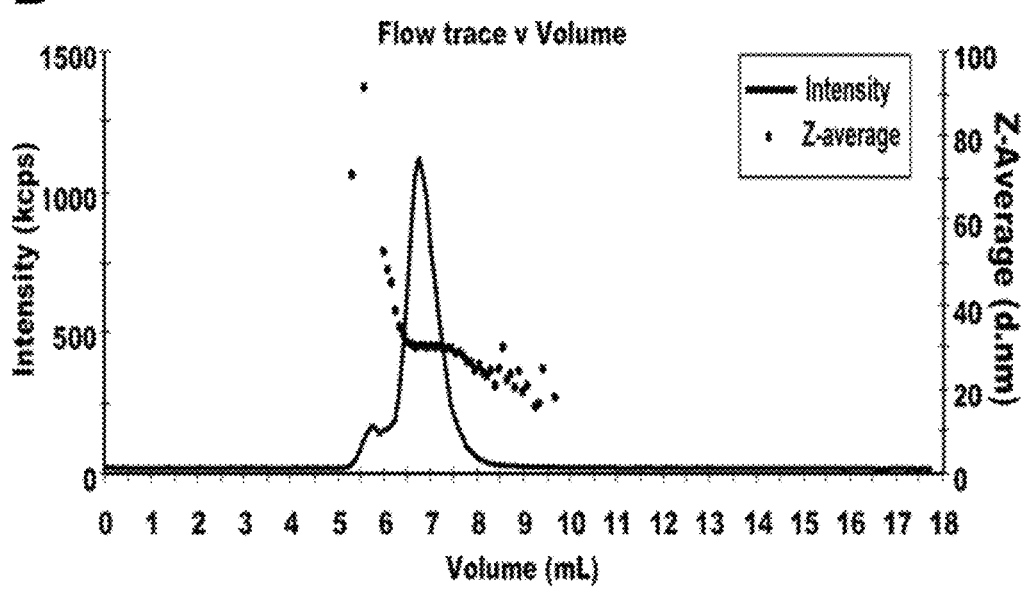

The light scattering intensity trace, as presented in FIG. 1B (solid line), recorded in the DLS detector also shows a single peak with a slight skew to the left in the same volume range. Z-average trace (dots) indicates that this peak is produced by particles with an average diameter of 29.28 nm.

This measurement is consistent with the known diameter of FMDV viral particle size. Table 2 lists the parameters output from the DLS analysis of the elution peak.

TABLE 2

DLS analysis of purified O1 Campos FMDV

| Peak | Start volume (mL) | End volume (mL) | Size (d · nm) | % Int. | DLS SD (d · nm) | Estimated MW (kDa) |
|---|---|---|---|---|---|---|
| 1 | 6.56 | 7.3 | 29.28 | 100.0 | 2.271 | 1800 |

Figure 2A:
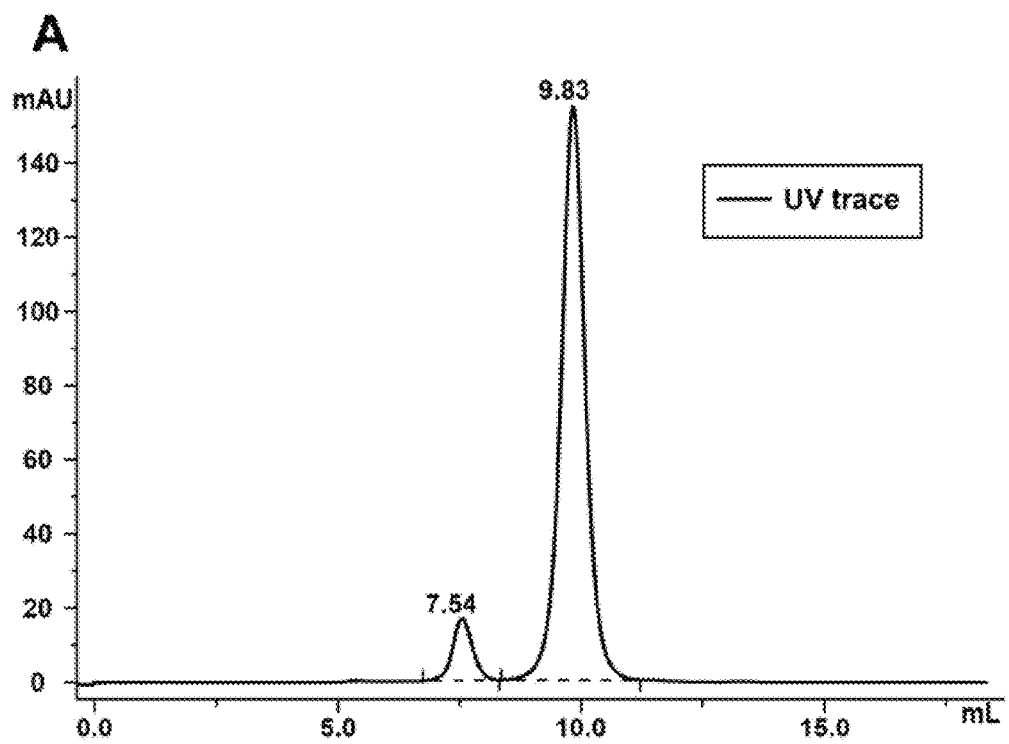
FIGS. 2A and 2B show one embodiment of the chromatographic profiles of purified O1 Campos FMDV after incubation at 56° C. for 1 hour and subsequent digestion with Benzonase®.

FIG. 2A shows the chromatographic profiles at U.V. 254 nm of purified O1 Campos FMDV after incubation at 56° C. for 1 hour and subsequent digestion with Benzonase®. Heat treatment at this temperature is known to disassemble the viral particle into 12S particles and/or capsomers and to expose viral RNA to nuclease digestion. Table 3 lists the parameters output from the UV chromatographic analysis of the elution peaks.

TABLE 3

Chromatographic parameters of purified O1 Campos FMDV after heat/enzyme treatment

| Peak | Elution Volume (ml) | Area (mAU * ml) | Height (mAU) |
|---|---|---|---|
| 1 | 7.54 | 2.6846 | 5.946 |
| 2 | 9.83 | 172.3857 | 265.774 |

The chromatographic profile at U.V. 254 nm of purified O1 Campos FMDV after heat/enzyme treatment showed two peaks, a small one at 7.54 mL and a big one at 9.83 mL. The peak observed on the chromatographic profile of the reference O1 Campos sample before treatment (elution volume 6.33 mL on FIG. 1A) has totally disappeared on this chromatographic profile.

Figure 2B:
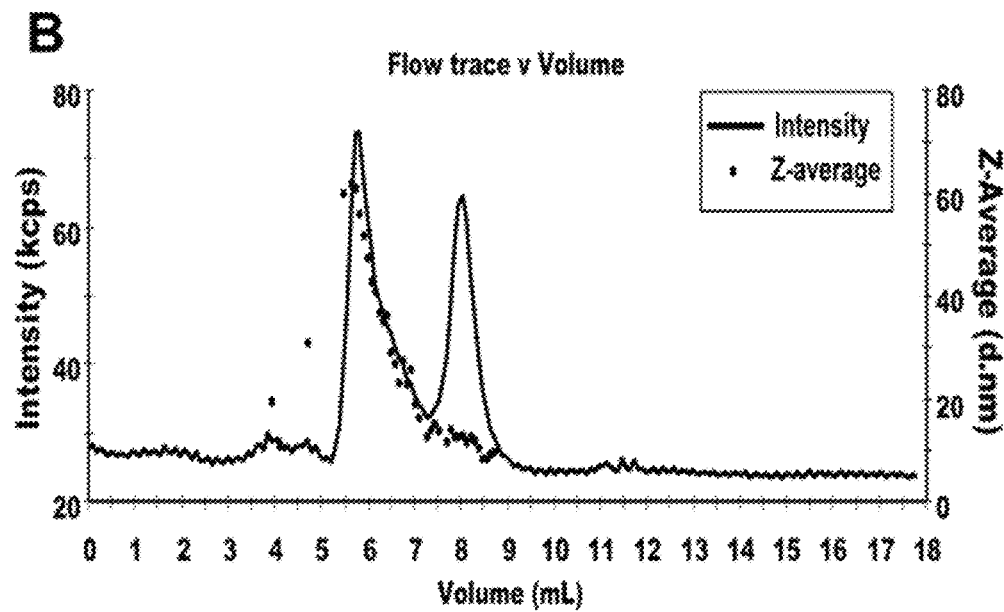

The light scattering intensity trace, as presented in FIG. 2B (solid line) in the DLS detector shows two signals. Table 4 lists the parameters output from the DLS analysis of the elution peaks.

TABLE 4

DLS analysis of purified O1 Campos FMDV after heat/enzyme treatment

| Peak | Start volume (mL) | End volume (mL) | Size (d · nm) | % Int. | DLS SD (d · nm) | Estimated MW (kDa) |
|---|---|---|---|---|---|---|
| 1 | 6.27 | 6.6 | 33.42 | 6.2 | 2.606 | 2450 |
| 2 | 7.21 | 9.48 | 13.03 | 93.8 | 1.371 | 270 |

The first one, between 6.27 mL and 6.6 mL of elution volume, represents only 6.2% of scattered light and did not correlate with significant U.V. detection. The Z-average trace showed for this peak a variable size ranging from 20 to 60 nm with a Z-average of 33.42 nm. As confirmed by the western blot analysis with antibodies against FMDV viral proteins, this peak was produced by the FMD virus particles which were not disintegrated upon treatment (data not shown).

The second intensity peak, with a Z-average diameter of 13.03 nm in the 7.21 to 9.48 mL of elution volume range, correlated with the smaller peak at 7.54 mL in the U.V. 254 nm profile. This peak produced intense signals in western blot analysis (data not shown). Based on size and reactivity, this peak was attributed to FMDV degraded fragments (12S particles and/or capsomers), which were 100% constituted of proteins and therefore displayed low absorption property at 254 nm (denoted by the peak at 7.54 ml in FIG. 2A).

The high peak eluted at 9.83 mL observed in the U.V. chromatography profile (FIG. 2A) was not detected by the DLS detector (FIG. 2B). This result was consistent with the ribonucleotides and/or oligoribonucleotides produced after Benzonase® digestion of the FMDV viral RNA genome.

Example 3

Effect of Chloroform Extraction and Benzonase Digestion on Quantification of FMDV Particles in a Viral Concentrate Prepared by PEG Precipitation This example illustrates the usefulness of the combined treatments of nuclease digestion and solvent extraction. In one embodiment, Benzonase® digestion was used to remove the contaminant cellular nucleic acids and chloroform extraction was used to clean up lipid contaminants.

Equipment and Operating Conditions:
Equipment, reagents and solutions used were the same as described in Example 2 except the following differences:
  Chromatograph: Akta Purifier UPC-10 form General Electric with 254/280 nm fixed wavelength UV and conductivity detectors with Unicorn control software.
  Dilution Buffer for PEG concentrated virus: 30 mM Tris, 100 mM NaCl, pH=8.
Analysis Procedure:
  Cell culture supernatant of BHK cells suspension cultures infected with O1 Campos FMDV strain were chemically inactivated and concentrated 50 times (50×) by precipitation by addition of a concentrated solution of PEG 6000, to reach a final PEG concentration of 5.5%. After 72 hours of precipitation, the supernatant is discarded and the 50×FMDV concentrate harvested.
  The harvested virus concentrate was subsequently diluted by 10 times with Dilution Buffer 30 mM Tris, 100 mM NaCl, pH=8 and magnetically stirred overnight at 4° C. to reduce the PEG concentration and allow the viral particles to get back into a soluble form.
a) Pre-Treatment of Samples
  Four different aliquots of the diluted FMDV concentrate sample were treated before the chromatographic run as follows:
  i) 5 mL of chloroform was added to 5 mL of sample and vigorously shaken to thoroughly mix. The mix was centrifuged to break the formed emulsion and the upper aqueous layer was recovered by pipetting.
  ii) 2 mL of sample was enzymatically digested with Benzonase® as described in Example 2.
  iii) 2 mL of aqueous aliquot recovered from aliquot i). was enzymatically digested with Benzonase® as described in Example 2.
  iv) 2 mL of sample were not treated, neither by chloroform extraction nor by enzymatic digestion.
  All four aliquots were centrifuged at 16000 g before the chromatographic analysis to eliminate any insoluble material and resulting supernatants were transferred to fresh tubes without disturbing the pellet.
b) Chromatographic Analysis
  Chromatographic analysis of all four aliquots was performed as described in Example 2. Injection volume was 100 μL and absorbance was monitored at 254 nm.

Interpretation of Results

Figure 3A:
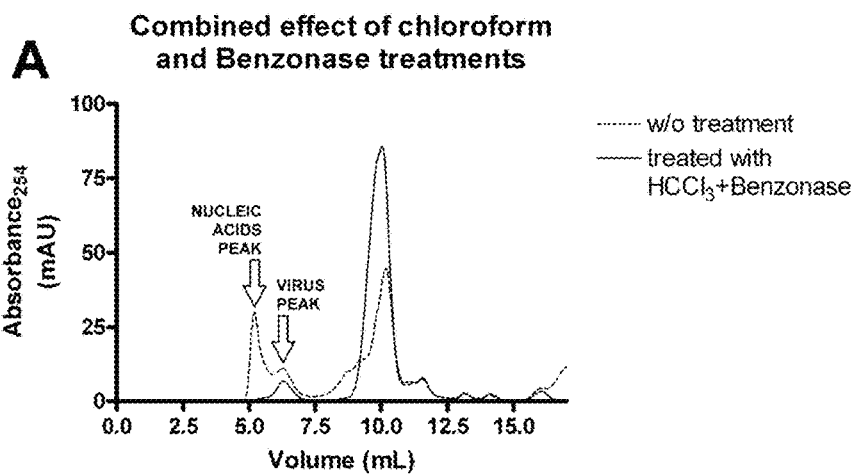
FIGS. 3A-3C show one embodiment of the effect of chloroform extraction and Benzonase® digestion on the quantification of FMDV particles in a viral concentrate prepared by PEG precipitation.
Figure 3B:
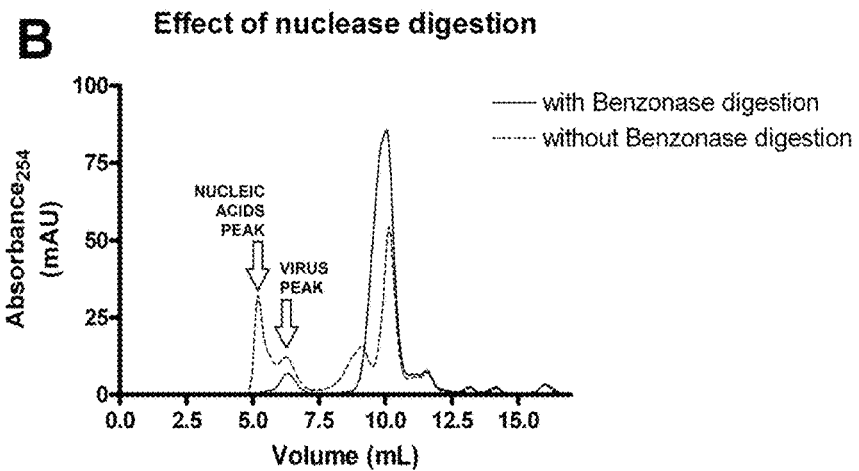
Figure 3C:
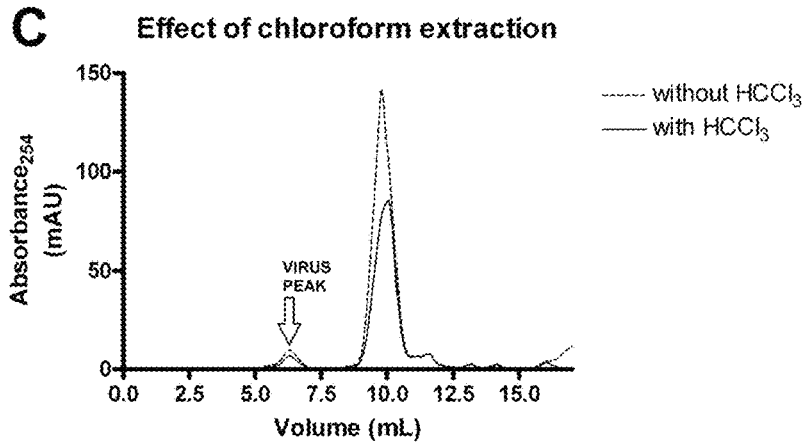

Results are shown in FIG. 3. In FIG. 3A, a comparison was made between untreated and fully treated samples. In the untreated sample, the virus peak was not resolved from the nucleic acid peaks and eluted as a "shoulder". In this case, accurate virus peak integration was not possible to achieve due to the nucleic acid contaminants. On the contrary, in the treated sample, the virus peak conformed to a symmetric "Gaussian bell" shaped peak that resolved to baseline. FIG. 3B illustrates the effect of omitting enzymatic treatment on chloroform extracted samples, showing that the main differences in virus peak shape was due to this digestion step. FIG. 3C highlights the point that even after enzymatic digestion, some high molecular weight lipid residues remained at the excluded volume. These lipid contaminants could be eliminated by chloroform extraction. Not performing this step may therefore lead to the overestimation of virus content in the sample.

Example 4

Determination of Stability of Vaccines Containing FMDV

This example illustrates one embodiment of the present invention for determining stability of a FMD vaccine.

Vaccines containing FMDV particles at an initial time and at later times after storage at 4° C. can be analyzed using the method as described herein. U.V. and DLS profiles obtained are analyzed for computing quantity and size of the FMDV particles. Change in number of FMDV particles upon storage can be interpreted in terms of percentage of the initial particles. Integrity of the FMDV particles can also be assessed by comparing the profiles obtained.

Example 5

Quantification and Characterization of FMDV Particles in High Concentration

This example illustrates the application of the present invention to a highly concentrated FMDV sample obtained by ultrafiltration. This example also illustrates the present application is capable of generating accurate measurement over a broad range of viral concentrations as indicated by the high linearity of viral concentration determined from various FMDV samples diluted from a high FMDV concentrate.

This example shows the capability of the present invention to consistently and accurately characterize the FMDV antigen size and integrity independent of the viral concentration.

Concentration of the antigens by ultrafiltration is a common process in FMD vaccine manufacturing. The infection of the cells in culture in bioreactors produces a low concentration material which is immediately inactivated by chemical inactivation. This material "as is" is not suitable for vaccine formulation partially due to its low viral particle concentration. To overcome this problem, one possible method is to use ultrafiltration procedures to increase viral particle concentration. During the concentration process, concentration and quality of the virus in the sample needs to be closely monitored in order to evaluate the process yields and integrity of the concentrated antigens. This example demonstrates that the present invention can be used with great accuracy to quantify the viral concentration from low concentration infection supernatant to high concentrates of FMDV particles, up to 150× and 727 µg/mL as tested in this example. In addition, in-line DLS detection is shown to be capable of characterizing the viral particle size and integrity with great accuracy and consistency across the full range of concentration of viral particles. This feature is particularly important during this type of concentration process as certain variable conditions of the process, like temperature, pH and the shear rate used could have dramatic impact on the viral particles integrity. Thus the present invention represents the ultimate tool of Process Analytical Technology (PAT) to ensure the success of the concentration step of the manufacturing process and to guarantee the quality of the concentrated antigen produced, no matter how high the final concentration is.

For this purpose, a viral suspension of O1 Campos strain concentrated by an ultrafiltration was used as a starting material for the response linearity assessment. The virus concentration of this viral suspension was estimated to be in the range of 700 to 800 µg/mL based on the initial volume of the viral suspension, volume reduction ratios and HPLC determinations along the ultrafiltration process. Three set of serial dilutions were prepared in three different days according to the dilution scheme shown in the Table 5. The three serial viral dilution samples were pre-treated and analyzed with duplicate injection for each sample using the method described in Example 2 using an Agilent 1260 Infinity chromatograph. Samples of both pure FMDV concentrate and dilution buffer were also analyzed. The buffer used for dilution of the sample has the following composition: 300 mM NaCl; 20 mM Tris Base; pH=8.

TABLE 5

Dilution scheme of FMDV concentration for the preparation of FMDV dilution samples.

| | Sample | | | | | |
| --- | --- | --- | --- | --- | --- | --- |
| | 0 | 1 | 2 | 3 | 4 | 5 |
| % of FMDV concentrate (by volume) | 0% | 20% | 40% | 60% | 80% | 100% |
| Volume of FMDV concentrate (µL) | 0 | 200 | 400 | 600 | 800 | 1000 |
| Volume of dilution buffer (µL) | 1000 | 800 | 600 | 400 | 200 | 0 |

Figure 4A:
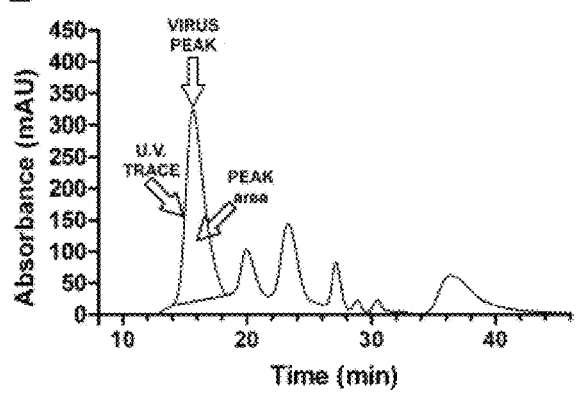
FIGS. 4A-4C show one embodiment of the quantification of a serial dilution of FMDV antigens which were prepared from an antigen concentrate obtained by an ultrafiltration concentration (UF).
Figure 4B:
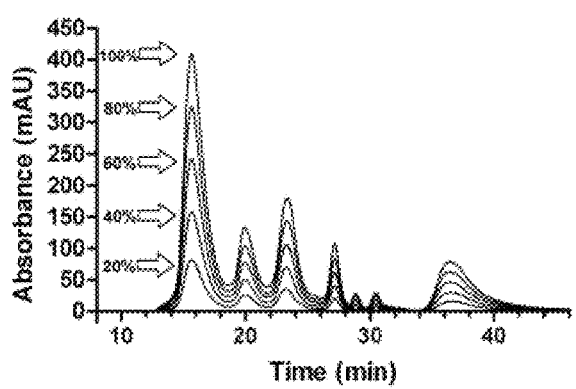
Figure 4C:
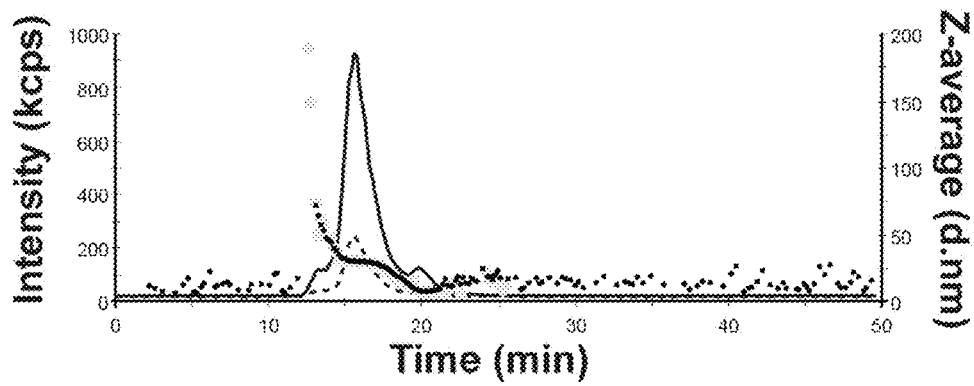
Figure 5:
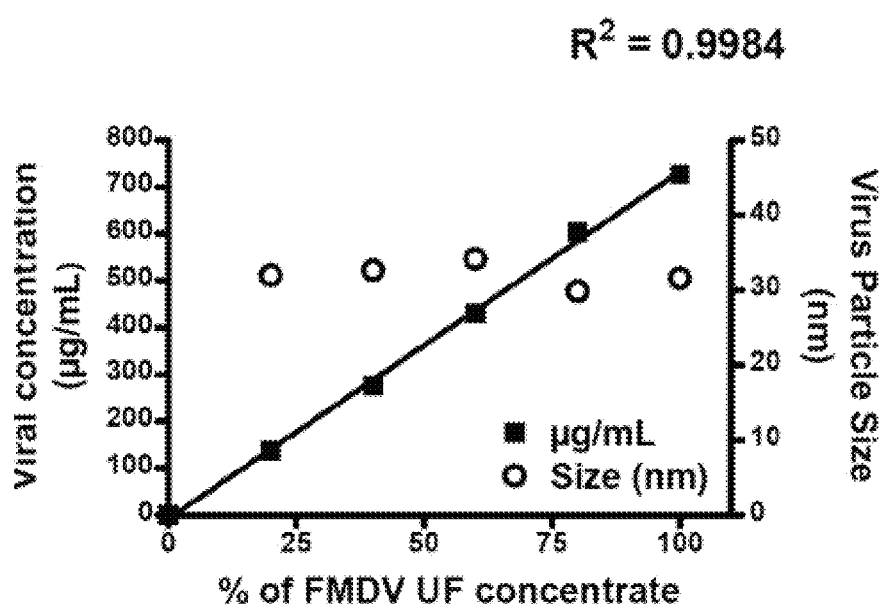

The resulting U.V. peak areas were analyzed and the FMD virus particles concentration was deduced for each sample. FIG. 4A shows the chromatographic profile tracked under 254 nm of a FMDV antigen concentrate obtained by the ultrafiltration. FIG. 4B shows the overlay of chromatographic profiles obtained from the five tested FMDV samples ranging from 20% to 100% of FMDV concentrate. Duplicate injection results were averaged for each set of serial dilution. The viral concentrations determined were plotted against percent concentration (FIG. 5). The final average of the three series was used to perform the regression analysis. As indicated in FIG. 5, a very high coefficient of determination $R^2$ (0.9984) was obtained showing a constant and robust association between the estimated viral concentration and the actual viral concentration of the sample, suggesting that the present invention can accurately estimate the viral concentration over a broad range of viral concentration. Dynamic light scattering data was continuously captured using a Malvern Nano S DLS instrument connected in-line with the HPLC at a sampling frequency of one reading every 10 seconds. Readings corresponding to the virus peak were singled out for Z-average diameter analysis in the Malvern Zetasizer software as shown in FIG. 4C. In-line DLS particle size determinations showed constant readings ranging from 29.9 to 34.2 nm and consistent with FMDV particle across all the concentration range assessed (see FIG. 5 and Table 6). All the results obtained from the analysis of ultraviolet and DLS traces is summarized in Table 6.

TABLE 6

Ultraviolet and DLS analysis of the three sets of serial dilution samples

| % FMDV concentrate by volume | $1^{st}$ serial dilution average (µg/mL) | $2^{nd}$ serial dilution average (µg/mL) | $3^{rd}$ serial dilution average (µg/mL) | Final average (µg/mL) | Z-average diameter (nm) |
|---|---|---|---|---|---|
| 0% | 0.0 | 0.0 | 0.0 | 0.0 | / |
| 20% | 145.3 | 131.8 | 133.2 | 136.8 | 32.0 |
| 40% | 283.0 | 273.6 | 273.9 | 276.8 | 32.7 |
| 60% | 433.7 | 432.7 | 424.9 | 430.4 | 34.2 |
| 80% | 581.0 | 629.2 | 600.2 | 603.5 | 29.9 |
| 100% | 730.4 | 761.3 | 689.3 | 727.0 | 31.6 |

Based on spectrophotometric error considerations it can be reasonably anticipated that concentrations that are two or three times as high as the one measured in this experiment can be accurately quantified with the present method, reaching the upper range of about 2250 µg/mL. This is based on the fact that photometric errors are quite low in the range of 100 mAU to 1500 mAU. It is also possible to inject a smaller sample volume, e.g. 50 µL instead of 100 µL or simply dilute the sample according to the anticipated concentration and correct the obtained result by the dilution factor. Accordingly, the present method can work on a concentration range that is well beyond the need of any practical manufacturing processes.

Dynamic Light Scattering detectors routinely work with protein samples in the order of 2 mg/mL or higher. So there is no doubt that the in-line DLS detection method described in the present invention would work perfectly well with samples with a higher concentration as the one describe in this example.

Typical concentration steps in FMD vaccine manufacturing processes reach concentrations that range from 10× to 60× of the virus concentration obtained during the infection step in cell culture. Nevertheless, when the objective is to produce a very highly concentrated FMD viral antigen bank, the concentration step can be continued until reaching concentration factor of 150× and even 200×. In this example, the highly concentrated virus material with a measured concentration of 727 µg/mL corresponds to a concentration factor of 150×. Although the upper limit for the concentration factor has to be determined case by case for each FMDV viral strain, it can be reasonably estimated that concentration of FMDV antigens up to 1250 µg/mL (or 1.25 mg/mL) or higher could be reached without causing negative impact on the solubility of the FMDV particles.

As demonstrated in this example, the method of the present invention is well suited to quantify and characterize the FMD viral particles in very highly concentrated samples and therefore can be applied to ultraconcentrated FMD antigen banks.

As a reference, usual virus concentration in vaccines varies according to virus strains, national regulatory agencies requirements and pharmacotechnical properties of the vaccine. The most common types of FMD vaccines are water-in-oil emulsions or water-in-oil-in-water double emulsions. The aqueous phases used to prepare the emulsions range in virus concentration from about 2 µg/mL to 60 µg/mL.

Example 6

Monitoring FMDV Infection in Industrial Cell Culture

This example shows the use of the present invention to monitor the course of infection in a 2000 liters industrial cell culture bioreactor.

For the FMDV infection step, 2000 L of BHK (Baby Hamster Kidney) cell suspension culture in GMEM (Glasgow Minimal Essential Medium) supplemented with 12% by volume of adult bovine serum were grown to a cell concentration of $2.4 \times 10^6$ cell/mL. Once this cell concentration was reached, the cells were allowed to sediment and the serum-containing medium was discarded and replaced by serum-free GMEM. Once re-suspended, the cell culture was inoculated with a O1 Campos FMDV seed culture at a MOI (multiplicity of infection) ranging from 0.001 to 0.05 viable viral particles per cell. Temperature was kept constant at 37° C. before and after infection. Culture samples were withdrawn at intervals of 1 hour up to the $4^{th}$ hour and every 30 minutes thereafter. Cell count was determined by microscopy counting in an Improved Neubauer hemocytometer. Remaining sample was centrifuged and the supernatant was directly analyzed using the present invention, in order to quantify the virus concentration and characterize its size and integrity.

The results of Example 6 are summarized in FIG. 6 and in Table 7.

TABLE 7

Change in concentration, size and cell count of virus during the 8-hours infection

| Hours after infection | Viral concentration (µg/mL) | Particle size (nm) | Cell count ($\times 10^6$ cell/mL) |
|---|---|---|---|
| 0 | 0.03* | | 2.38 |
| 1.0 | 0.01* | | 2.52 |
| 2.0 | 0.01* | | 2.56 |
| 3.0 | 0.01* | | 2.78 |
| 4.0 | 0.12* | | 2.80 |
| 4.5 | 0.18* | | 2.58 |
| 5.0 | 0.19* | | 2.54 |
| 5.5 | 0.25* | | 2.16 |
| 6.0 | 1.22 | 31.0 | 2.06 |
| 6.5 | 2.72 | 32.3 | 1.20 |
| 7.0 | 3.85 | 33.4 | 0.60 |
| 8.0 | 5.20 | 34.7 | 0.06 |

*Those values are below the current limit of detection of the validated technique and therefore cannot be taken in this example as significantly different from the background noise.

Up to the $4^{th}$ hour after infection, cells continue to grow but no or very little virus was detected. From hour 4 to hour 6.5, virus could be detected by the U.V. detector but the signal was too low to enable an accurate DLS reading. From hour 6.5 onwards, virus was easily detectable with both U.V. and DLS detectors. The in-line DLS detector produced readings of 31-35 nm, which were fully consistent with the described diameter of FMDV.

This example shows how the quantification and the characterization technique of the present invention can perform at a very low concentration range of FMD virus particles. The U.V detector started to provide reliable readings at 254 nm at 6 hours after the beginning of the infection of the cell culture (measurement superior to 1 µg/mL, which is the current validated limit of detection (LOD)). Surprisingly, the DLS detector started to provide reliable and consistent measurement of the size of the FMDV particles at a starting concentration of 1.2 µg/mL. This represents an important feature of the present invention as the working protein concentration usually described for a normal operation of DLS detectors is in the range of 0.5 to 2 mg/mL, several orders of magnitude higher that the viral concentrations described in this example. Furthermore, with the pre-treatment steps using solvent and nucleases, the present invention can remove the large interfering contaminants from the sample and obtain FMDV particles with high purity for quantification and characterization. Other technologies such as SEC alone likely elute the virus and the large contaminants within a similar range of elution volumes and therefore cannot sufficiently purify and analyze the virus.

Also this example demonstrates that the technique of the present invention can be applied to live FMD virus particles. These data, together with the rest of the data of the present invention, further prove that the described technique can be used at absolutely every single step of manufacturing process of an FMD vaccine, no matter if the virus is still alive or if it has been already inactivated.

Finally, it can be reasonably anticipated that the use of more modern U.V. detectors, such as detectors having a bigger optical path or reduced background level, would enable to further decrease the limit of detection (LOD) and the limit of quantification (LOQ) of the present invention to, for example a LOD of 0.1 µg/mL and a LOQ of 0.3 µg/mL.

Example 7

Column-Switching System

In one embodiment, the present invention provides a method of high-throughput quantification and characterization of Foot and Mouth Disease Virus (FMDV).

Due to the nature of the size exclusion chromatography, it is usually necessary to completely elute all the peaks from the previous sample before starting a new round of chromatography for another sample. Therefore, FMDV antigens having a large molecular weight can be quantified during the first half of a chromatographic run, but the analysis of the next sample cannot be started until the low molecular weight components of the previous sample are completely eluted from the column. Otherwise, the virus peaks of the next sample may superimpose with the trailing peaks from the previous run sample, thereby leads to a contamination. Data captured within this time frame is useless to the purpose of quantifying virus content or determining antigen integrity. The time required to elute all the low molecular components can be regarded as unproductive idling of equipment and operator time which ultimately reduces the overall productivity of the analytical laboratory.

It is possible to increase the productivity by setting up another full HPLC system with its own pair of UV and DLS detectors but this can be very expensive and inconvenient due to space constraints in FMDV vaccine manufacturing QC laboratories. The present invention provides a column-switching system which is able to reduce the expense of having duplicated UV and DLS detectors and keep the equipment footprint at almost the same as the single column configuration.

Figure 7:
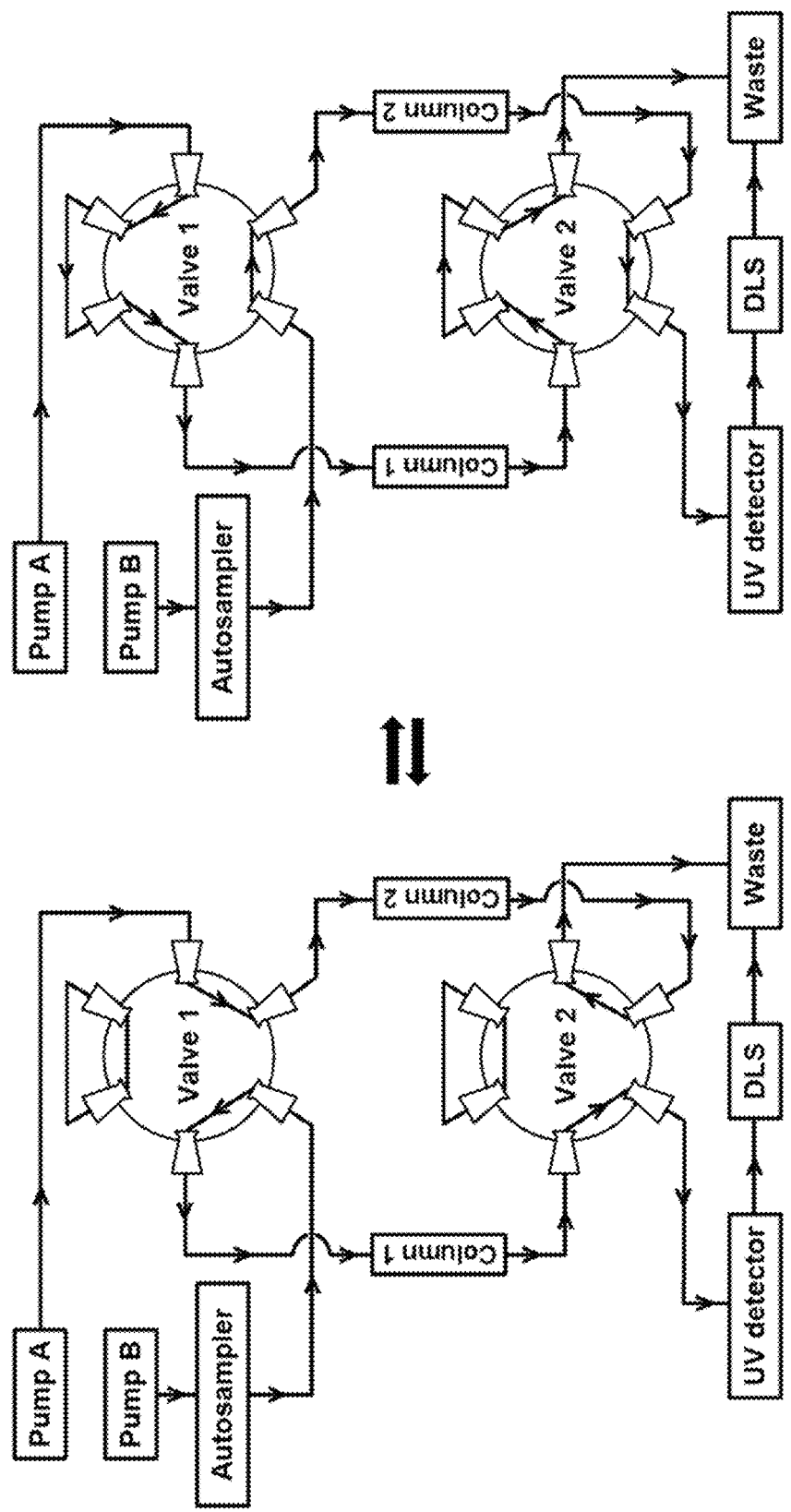
FIG. 7 shows one embodiment of the schematics of a column-switching system which runs a Dynamic Light Scattering (DLS) detector and two size-exclusion chromatography (SEC) columns in parallel. The setups on the left and right panels can be switched back and forth.

In one embodiment, the present column-switching system is configured to include a two-valve array, two HPLC pumps, two SEC columns, one U.V. detector and one DLS detector. In another embodiment as illustrated in FIG. 7, the system further includes components such as an autosampler and a waste collector. This setup is feasible to cut the chromatography run time by half and therefore effectively doubles the productivity. It should be noted that the present column-switching system can take any suitable forms and be configured with various features and components according to the need of the quantification and characterization. For example, one may connect three HPLC pumps, three SEC columns and one DLS detector for running three batches of sample simultaneously.

As illustrated in FIG. 7, the two-valve array includes valve 1 and valve 2 which can be connected to different system components such as the pump, the autosampler, different types of columns, UV detectors and the waste collector. The two valves can be independently controlled or operated together to implement the present column-switching system.

Before running, samples to be analyzed are put into the autosampler. Appropriate buffers such as the equilibration buffer and wash buffer are put under the two pumps.

As shown in the left panel of FIG. 7, while a sample is running in Column 1 using Pump B, Column 2 is being washed and equilibrated with appropriate buffer from Pump A. After the virus peak is eluted and quantified in the UV detector and the size and integrity of the obtained virus elution is assessed in the DLS detector, the valve array is switched to the position shown in the right panel of FIG. 7.

The analysis of the next queued sample in the autosampler can then be started immediately in Column 2. Meanwhile, any low molecular weight components remaining in Column 1 that are of no interest can be flushed directly to Waste under the equilibration by Pump A. For the following samples, valve array is switched back and forth and analysis of samples eluted alternates from Column 1 and Column 2 until all samples in the autosampler are exhausted.

In one embodiment, the valves are controlled by the same software that controls and integrates the functioning of other system components such as the pumps and autosamplers, or software that captures data from the UV and DLS detectors. In one embodiment, Agilent ChemStation Software which controls Agilent 1260 Infinity chromatograph was used to control the whole system. It is also possible to pre-set programs to implement a fully-automated process which includes but is not limited to the following steps: equilibration and washing of the column, injection of sample to the column, performing size-exclusion chromatograph with UV profile tracked, and quantification, characterization of the eluted peak using a U.V. detector and DLS detector, and waste removal from the column. Other automated or robotic system can also be used to perform steps such as the solvent (e.g. chloroform) extraction and enzymatic digestion in the pre-treatment step to further improve the efficiency of the quantification and characterization.

In one embodiment, operation of the system is tightly controlled by suitable software and system. For example, software and system that produce, integrate and analyze the UV and DLS chromatographs can be used to convert the chromatographic data of each eluted fraction to analytical data in a real-time manner for an easier interpretation. Warning systems for common error conditions (e.g. leakages, overpressure) and remote control system can also be included in the present system.

This example clearly shows that the implementation of the multi-column switching system further enhances the throughput of the analysis. The whole system demonstrates many synergistic characteristics that greatly improve the efficiency of the analysis of FMDV antigens; namely, elimination of the interference of large DNA molecules by endonuclease digestion, elimination of the interference of large lipid residues by solvent (e.g. chloroform) extraction, separation of low molecular weight molecules by SEC, elution of the virus particles in the exclusion volume (or near exclusion volume) of the SEC column, simultaneous run of two or more SEC and real-time DLS analysis. The present invention is capable of producing a pure segregated FMD virus peak and analyzing the eluted peak by the U.V. detector and the DLS detector in 20 minutes after the start of the chromatographic run. The present invention does not only achieve a high-throughput but also a more cost-effective analysis of FMDV antigens because the switching system does not require multiple DLS detectors and thereby minimizes the working space for setting up the whole system.

In one embodiment of the present SEC, the FMDV peak is eluted at around 20 minutes after the injection of the sample and the whole chromatography takes about 50 minutes to elute all the low and high molecular molecules from the column. Accordingly, one sample can be loaded on one column every 50 minutes for a new round separation.

In one embodiment of the present invention in which the column-switching system is implemented, analysis of the next sample can be done after the first 20-minutes analysis of the first sample and thereby maximizes the use of machinery and time. It is estimated that the present invention can complete the purification, quantification and characterization of at least 57 samples per day.

In one embodiment of the present column-switching system comprising two SEC columns, when one sample is loaded to each of the column every 50 minutes, the two columns can handle about 57 samples in every 24 hours.

In one embodiment, the present column-switching system comprises three HPLC pumps, three SEC columns, one U.V. detector and one DLS detector. Since virus peak is eluted at around 20 minutes after the sample injection, the three columns together with the U.V. and DLS detectors can handle 3 samples per hour. In this case, one sample is loaded on each of the column every 60 minutes. The two detectors recorded and analyze signals of virus eluted from the first column, and then the virus eluted from the second column and finally from the third column. After the virus peak has been eluted from the column number 3, the system switches back to column number 1 to load the next sample. Therefore, the system can handle and analyze about 72 samples in every 24 hours.

In additional to the capability of handling all types of samples from crude samples to highly purified and concentrated samples, the present invention clearly provides a very versatile, sensitive and high-throughput analysis that cannot be achieved by any current technologies such as FPLC and the 146S sucrose gradient technique.

In summary, the present invention provides methods and systems that can isolate FMD virus and antigens in high purity, quantify and characterize these products with high sensitivity and accuracy within a very short time. Clearly, the present invention permits a very high-throughput analysis of FMDV products to meet the high demand in both the quantity and quality of FMDV vaccines.

What is claimed is:

1. A method for quantification and characterization of Foot and Mouth Disease Virus (FMDV), comprising the steps of:
   a) treating samples comprising FMDV with one or more enzymes to obtain a plurality of FMDV samples;
   b) applying a first FMDV sample to a chromatographic system comprising a plurality of pumps and a plurality of chromatographic columns, wherein
      i. a first pump is connected to a first chromatographic column via a first valve, said first column is further connected via a second valve to a detection system comprising a Dynamic Light Scattering (DLS) detector and an UV detector, and
      ii. a second pump is connected to a second chromatographic column via said first valve, said second column is further connected via said second valve to a waste collector,
      wherein the first FMDV sample is run through the first column while a washing buffer is run through the second column;
   c) eluting the first FMDV sample from the first column and obtaining chromatographic profiles for quantification and characterization of the first FMDV sample by said detection system;
   d) switching connections for said first and second pumps so that
      i. said first pump is now connected to said second column via said first valve, said second column is further connected via said second valve to said detection system; and
      ii. said second pump is now connected to said first column via said first valve, said first column is further connected via said second valve to a waste collector,
   e) applying a second FMDV sample to the second column while applying a washing buffer to the first column;
   f) eluting said second FMDV sample from said second column and obtaining chromatographic profiles for quantification and characterization of said second FMDV sample by said detection system; and
   g) repeating the steps of (b) to (f), thereby obtaining quantification and characterization of said plurality of FMDV samples.

2. The method of claim 1, wherein the enzyme is endonuclease, exonuclease, restriction enzyme, DNase or RNase.

3. The method of claim 1, wherein the samples comprising FMDV in step (a) are selected from the group consisting of supernatant of FMDV-infected cell cultures, an intermediate product from a vaccine manufacturing process, an antigen batch or bank, a vaccine, a monovalent vaccine batch, and a multivalent vaccine batch.

4. The method of claim 1, wherein the samples comprising FMDV are treated in a solvent before or after treating with said one or more enzymes in step (a).

5. The method of claim 4, wherein the solvent is a non-polar solvent selected from the group consisting of chloroform, benzene, toluene, hexane, pentane and octane.

6. The method of claim 1, wherein the chromatographic system comprises two chromatographic columns.

7. The method of claim 1, wherein the chromatographic system comprises three chromatographic columns.

8. The method of claim 1, wherein the chromatographic columns are designed to separate particles with sizes in the range of 20-200 nm and molecular weights in the range of $10^5$-$10^9$ Dalton.

9. The method of claim 1, wherein the chromatographic profile is compared to a chromatographic profile derived from a reference sample of purified FMDV, or compared to a chromatographic profile derived from whole integral viral particles to allow differentiation of whole integral viral particles from disintegrated FMDV fragments.

10. The method of claim 1, wherein the method is capable of analyzing the chromatographic profiles of about 60 to about 70 samples per day.

\* \* \* \* \*